United States Patent [19]

Coutts et al.

[11] 4,166,116
[45] Aug. 28, 1979

[54] PHARMACEUTICAL COMPOSITIONS CONTAINING PIPERAZINYL ACYLHYDROXAMIC ACID DERIVATIVES TO TREAT INFLAMMATION OR ANAPHYLACTIC ALLERGY CONDITIONS

[75] Inventors: Ronald T. Coutts, Edmonton; David F. Biggs, Sherwood Park; Frank W. Wandelmaier, Montreal; Frank D. Semaka, Calgary, all of Canada

[73] Assignee: Canadian Patents and Development Limited, Ottawa, Canada

[21] Appl. No.: 850,825

[22] Filed: Nov. 11, 1977

[51] Int. Cl.$^2$ ............................................. A61K 31/495
[52] U.S. Cl. ...................................................... 424/250
[58] Field of Search ............................................ 424/250

[56] References Cited
PUBLICATIONS

Jour. Med. Chem., vol. 12, p. 940, (1969).
Semaka, Thesis–University of Alberta, Edmonton, Canada, Spring 1974.

Primary Examiner—Stanley J. Friedman
Attorney, Agent, or Firm—Alan A. Thomson

[57] ABSTRACT

Compounds of the following general formula have been found to have biological activity and are useful in pharmaceutical compositions:

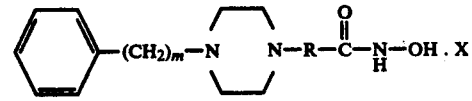

wherein
m = 0, 1 or 2
R = alkylene straight or branched chain of up to 3 carbon atoms, and
X when present is a salt-forming acid.

Typical compounds are 2-methyl-3-{1-(4-phenyl) piperazinyl} propionohydroxamic acid monohydrochloride and {1-(4-phenethyl) piperazinyl} acetohydroxamic acid dihydrochloride. These compounds have been found to have at least one of anti-inflammatory, anti-anaphylactic and anti-depressant activity.

15 Claims, No Drawings

PHARMACEUTICAL COMPOSITIONS CONTAINING PIPERAZINYL ACYLHYDROXAMIC ACID DERIVATIVES TO TREAT INFLAMMATION OR ANAPHYLACTIC ALLERGY CONDITIONS

FIELD OF THE INVENTION

This invention is directed to derivatives of piperazinyl-acylhydroxamic acids and their salts in pharmaceutical compositions including the compounds as active ingredient. The compounds have at least one of anti-inflammatory, anti-anaphylactic and anti-depressant activity. The therapeutic use of these compounds is also described.

PRIOR ART AND BACKGROUND

References have been noted to piperazinyl compounds (and ethers thereof); aryl- or aralkyl-substituted piperazinyl ether, hydroxyl or nitrile compounds, and piperazinyl ester derivatives, some of which have biological activity. Acylhydroxamic acid derivatives have been described in the literature including pyridinium and piperidinium derivatives.

No reference to piperazinyl, particularly aryl- or aralkyl-piperazinyl, derivatives of acylhydroxamic acids has been noted, except the one non-aromatic compound N,N'-piperazinyl-bis-(isoproprionohydroxamic acid) reported in Jour. Medicinal Chem., Volume 12, page 940 (1969) by R. T. Coutts et al. The only significant biological activity found for this latter compound was a hypotensive effect.

SUMMARY OF THIS INVENTION

We have found that the aromatic-substituted piperazinyl acylhydroxamic acid compounds having the following general formula:

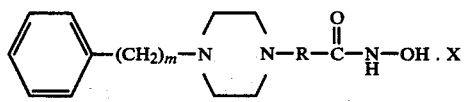

where
 m=0, 1 or 2
 R=alkylene straight or branched chain of up to 3 carbon atoms, and
 X when present is a salt-forming acid,
have useful therapeutic activity as anti-inflammatory, anti-anaphylactic or anti-depressant agents. The aromatic-containing substituent on the piperazine ring is selected from phenyl, benzyl and phenethyl. The acyl moiety is selected from aceto, propiono (including isopropiono) and butyro (including isobutyro). The compound is usually but not necessarily isolated in the form of its mono- or di-salt, the salt-forming acids preferably being selected from hydrochloric acid, hydrobromic acid and oxalic acid.

These compounds have been found to have at least one biological activity from among anti-inflammatory, anti-anaphylactic, and anti-depressant.

The invention includes a method of treating inflammation, anaphylactic allergy conditions or depression comprising administering to an animal subject to at least one of these conditions, a piperazinyl acylhydroxamic acid derivative having the following general formula:

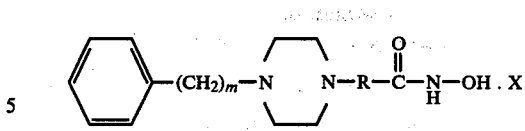

where
 m=0, 1 or 2
 R=alkylene straight or branched chain of up to 3 carbon atoms, and
 X when present is a salt-forming acid,
the compound being administered in sufficient amounts to bestow anti-inflammatory, anti-allergic or anti-depressant activity.

The compounds may be suitably prepared by the method comprising the steps (a), (b) and (c).

(a) Preparation of 1-monosubstituted-piperazines (II) by a literature method (D. K. Yung, L. G. Chatten and D. P. Macleod, J. Pharm. Sci., 57, 2073–2080 (1968) and characterization of each 1-monosubstituted piperazine by its boiling point and infrared spectrum.

(b) Preparation of aminoesters of general structure (III) by either (i) reacting the 1-monosubstituted-piperazine (II) with methyl or ethyl acrylate, with methyl crotonate and with methyl methacrylate.

or (ii) by reacting the 1-monosubstituted-piperazine (II) with ethyl chloroformate, or ethyl bromoacetate or ethyl 4-bromobutyrate, each in the presence of triethylamine.

All the aminoesters (III) were converted to their mono- or di-hydrochlorides by reacting each methyl ester with a methanolic solution of dry hydrogen chloride, and each ethyl ester with an ethanolic solution of dry hydrogen chloride.

The structures of all the aminoester (III) mono- or di-hydrochlorides were verified by microanalysis, and by means of their infrared and nuclear magnetic resonance spectra.

(c) Preparation of piperazinyl acylhydroxamic acids (I) by reacting the aminoester (III) free base with hydroxylamine and/or hydroxylamine hydrochloride in methanol using literature methods (W. N. Fishbien, J. Daly and C. L. Streeter, Anal. Biochem., 28 13–24 (1969); R. T. Coutts, K. K. Midha and K. Prasad, J. Med. Chem., 12, 940–941 (1969); R. T. Coutts, J. W. Hubbard, K. K. Midha and K. Prasad, J. Pharm Sci., 68, 28–33 (1971)).

The piperazinyl acylhydroxamic acids (I) were obtained as their mono- or di-hydrochlorides as colorless solids. Their structures were confirmed by microanalysis, infrared and nuclear magnetic resonance spectroscopy, and by means of a color reaction with alcoholic ferric chloride solution.

The preparation of numerous examples of aminoester (III) salts and piperazinyl acylhydroxamic acid (I) salts are described in detail in the Ph.D. thesis of Frank D. Semaka (University of Alberta, Edmonton, Canada), Spring 1974, supervised by Drs. David T. Biggs and Ronald T. Coutts.

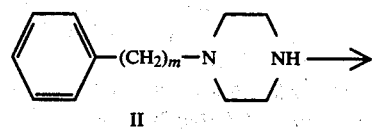

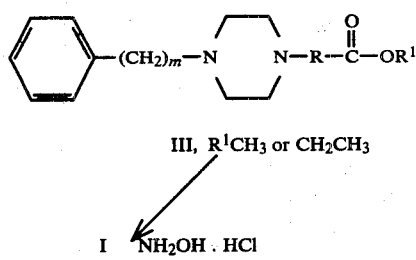

III, R¹CH₃ or CH₂CH₃

I, NH₂OH . HCl

The following seven typical compounds were prepared as described above as examples.

2-Methyl-3-{1-(4-phenyl)piperazinyl}propionohydroxamic Acid Monohydrochloride A1
2-Methyl-3-{1-(4-phenethyl)piperazinyl}propionohydroxamic Acid Monohydrochloride A2
3-Methyl-3-{1-(4-phenyl)piperazinyl}propionohydroxamic Acid Dihydrochloride A3
4-{1-(4-Phenyl)piperazinyl}butyrohydroxamic Acid Monohydrochloride A4
3-{1-(4-Phenyl)piperazinyl}proprionohydroxamic Acid Monohydrochloride A5
4-{1-(4-phenethyl)piperazinyl}butyrohydroxamic Acid Dihydrochloride A6
{1-(4-Phenethyl)piperazinyl}acetohydroxamic Acid Dihydrochloride A7

Biological Activity of Typical Compounds

The typical compounds A1 to A7 were tested in animals as follows.

Initially the activity of the compound tested on an animal was determined at a single dose. If the substance was active at this dose, it was subjected to limited repeat testing. If the presence of activity was confirmed by repetition of the testing, a dose response relation was constructed and the effective dose (ED₅₀) determined. If toxicity was encountered with the initial dose, the dose was reduced until a dose was reached which was tolerated by the animals being tested.

Compounds of the general formula I have been found to possess anti-inflammatory, anti-anaphylactic or anti-depressant action in animals.

EXAMPLE 1

Anti-Inflammatory Activity

The compounds were administered subcutaneously, as a solution in physiological saline, to female Sprague-Dawley rats, weighing 100–120 g. A suspension of 0.03% carrageenan was injected under the plantar skin of a hind paw. The increase in volume of the inflamed paw was measured 3 and 5 hours after drug administration. The percent inhibition of edema volume compared to the vehicle-treated control group was calculated. Results are summarized in Table 1. Phenylbutazone* and tolmetin**, known anti-inflammatory agents, were used as controls and for comparison.

Reference: Winter C. A. (1965) in *International Symposium on Non-Steroidal Anti-Inflammatory Drugs*, edit: Garattini, S. and Dukes M. N. G. pp. 190–202, Excerpta Medica Foundation, Amsterdam.
*Phenylbutazone: 4-butyl-1,2-diphenyl-3,5-pyrazolidinedione.
** Tolmetin: sodium 1-methyl-5-p-toluoyl pyrrole-2-acetate dihydrate.

Table 1

| | | | ANTI-INFLAMMATORY ACTIVITY: | | | |
|---|---|---|---|---|---|---|
| | | | Response % Inhibition | | ED₅₀* | 95% confidence |
| Substance | Dose mg/kg | No. of Animals | 1 hr. | 3 hrs. | mg/kg | limits |
| A-1 | 64 | 4 | 23.5 | 15.4 | — | — |
| A-2 | 64 | 4 | 67.7 | 39.6 | — | — |
| A-4 | 8 | 4 | 37.3 | 0 | | |
| | 16 | 4 | 66.6 | 19.3 | | |
| | 32 | 4 | 64.5 | 0 | 15 | (5.1–44.3) |
| | 64 | 4 | 84.0 | 6.3 | (1 hour post-treatment) | |
| | 128 | 4 | 85.6 | 0 | | |
| A-5 | 32 | 4 | 55.1 | 41.2 | — | — |
| A-6 | 64 | 4 | 65.0 | 16.4 | — | — |
| A-7 | 8 | 4 | 56.0 | 25.2 | | |
| | 16 | 4 | 40.5 | 11.4 | | |
| | 32 | 4 | 57.6 | 8.5 | 13 | (2.1–80.5) |
| | 64 | 4 | 74.8 | 8.8 | (1 hour post-treatment) | |
| | 128 | 4 | 79.9 | 16.7 | | |
| Phenylbutazone | 50 | 4 | 48.5 | 64.0 | — | |
| Tolmetin | 150 | 4 | 60.6 | 91.4 | — | |

*Determined by the method of Litchfield and Wilcoxon (J. Pharmacol. Exp. Therap. 96: 99, 1949)

EXAMPLE 2

Anti-Anaphylactic Activity

Sprague-Dawley rats weighing 100–125 g, sensitized by intradermal injection of different concentrations of anti-sera, were treated intravenously with a combination of egg albumin and Evan's blue dye to produce visible, localized, anaphylactic reactions at the sites of dermal sensitization. The ability of intravenously administered substances to inhibit the reaction was determined. Results with disodium chromoglycate, a known anti-anaphylactic, are shown for comparison. The substances were in physiological saline. Reference: Goose, J. and Blair, A. M. J. N. Immunology 16: pp. 749–760 (1969).

Table 2

| Substance | Dose (mg/kg) | No. of animals | Response % inhibition | |
|---|---|---|---|---|
| A-1 | 50 | 4 | 72 | |
| | 100 | 4 | 96 | |
| | 100 | 4 | 91 | 93.5 aver. |
| A-2 | 100 | 4 | 60 | |
| | 100 | 4 | 78 | 69.0 aver. |
| Disodium-chromoglycate | 100 | 8 | 72 | |

Anti-Depressant Activity

The compounds, dissolved in physiological saline, were administered intraperitoneally to Swiss Albino mice, of either sex, weighing 18–22 g. Thrity minutes later, the mice were treated with 5 mg/kg reserpine, given subcutaneously. The degree of ptosis was evaluated 120 minutes after reserpinization. The response was expressed as percent animals protected. Animals with completely open to half-open eyes were considered protected. For comparison, the $ED_{50}$ is shown for amitriptyline, a known anti-depressant. Typical results are shown in Table 3. Reference: Rubin et al. J. Pharmacol. Exp. Therap. 120: 125 (1957).

Compounds of the general formula I may be useful in the treatment of one or more of arthrites, inflammation, depression, asthma or allergic conditions.

The compounds are absorbed orally and may be administered by the oral route in the form of tablets, sugar-coated pills, capsules, gelules, or oral drops; by parenteral means as an injection prepared by dissolving or suspending the compounds in a therapeutically acceptable carrier preferably physiological saline; or by the rectal route in the form of a suppository.

They may also be applied topically, for inflammation or allergic conditions, in the form of a cream, lotion or ointment, a dry powder applied as such (or inhaled for asthma treatment) while in a therapeutically and physiologically-acceptable carrier.

The usual concentration range of the active compounds in the carrier composition is about 0.1–10% wt. but this is not critical. The dosage can vary considerably depending on the compound, the animal species and other variables. In most instances, the dose will be an effective amount below about 50 mg/kg body wt. In some cases, from about 1–10 mg/kg will be sufficient.

Accordingly, the present invention comprises a therapeutic composition made up of a compound of the general formula I, together with a physiologically-acceptable carrier, and the method of use thereof as a therapeutic treatment.

Table 3
ANTI-DEPRESSANT ACTIVITY:

| Substance | Dose mg/kg | No. of Animals | Response Anim. Protected 120 min.(%) | $ED_{50}$* mg/kg | 95% confidence limits |
|---|---|---|---|---|---|
| A-1 | 4 | 6 | 34 | | |
| | 8 | 6 | 50 | | |
| | 16 | 12 | 50 | 7.4 | (4.1–13.3) |
| | 24 | 12 | 75 | | |
| | 32 | 12 | 92 | | |
| A-3 | 8 | 6 | 17 | | |
| | 16 | 6 | 17 | | |
| | 32 | 6 | 50 | 32 | (17.4–58.9) |
| | 64 | 6 | 83 | | |
| A-5 | 64 | 6 | 67 | — | |
| A-7 | 128 | 6 | 33 | — | |
| Amitriptyline | — | — | — | 2.4 | (1.5–3.8) |

*Determined by the method of Litchfield and Wilcoxon (J. Pharmacol. Exp. Therap. 96: 99, 1949)

We claim:

1. A method of treating inflammation or, anaphylactic allergy conditions comprising administering to an animal subject to at least one of these conditions a piperazinyl acylhydroxamic acid derivative having the following general formula

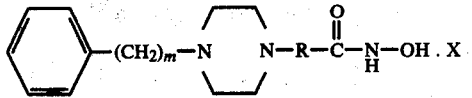

where
m=0, 1, or 2
R=alkylene straight or branched chains of up to 3 carbon atoms, and
X when present is a salt-forming acid,
the compound being administered in sufficient amounts to bestow anti-inflammatory or, anti-allergic activity.

2. The method of claim 1 wherein the compound is administered parenterally in a physiologically acceptable liquid carrier.

3. The method of claim 1 wherein the compound is selected from the group consisting of:

2-methyl-3-{1-(4-phenyl)piperazinyl}propionohydroxamic acid
2-methyl-3-{1-(4-phenethyl)piperazinyl}propionohydroxamic acid
3-methyl-3-{1-(4-phenyl)piperazinyl}propionohydroxamic acid
4-{1-(4-phenyl)-piperazinyl}butyrohydroxamic acid
3-{1-(4-phenyl)-piperazinyl}propionohydroxamic acid
4-{1-(4-phenethyl)-piperazinyl}-butyrohydroxamic acid
{1-(4-phenethyl)-piperazinyl}acetohydroxamic acid or hydrochloride salts thereof.

4. A therapeutic composition comprising a physiological saline pharmaceutical carrier; and piperazinyl acylhydroxamic acid derivatives having the following general formula:

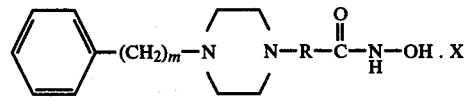

where
m=0, 1 or 2
R=alkylene straight or branched chain of up to 3 carbon atoms, and X when present is a salt-forming acid, the compound being present in sufficient amounts to bestow anti-inflammatory or anti-anaphylactic allergy activity.

5. The composition of claim 4 wherein the compound's phenyl or phenalkyl moiety is one of phenyl, benzyl and phenethyl.

6. The composition of claim 4 wherein the compound's acyl moiety is one of aceto, propiono and butyro.

7. The composition of claim 4 wherein the salt-forming acid X is present as the mono- or di-hydrochloride.

8. A composition of claim 4 including 2-methyl-3-{1-(4-phenyl)piperazinyl}propionohhydroxamic acid or hydrochloride salt thereof.

9. A composition of claim 4 including 2-methyl-3-{1-(4-phenethyl)piperazinyl}propionohydroxamic acid or hydrochloride salt thereof.

10. A composition of claim 4 including 3-methyl-3-{1-(4-phenyl)piperazinyl}propionohydroxamic acid or hydrochloride salt thereof.

11. A composition of claim 4 including 4-{1-(4-phenyl)piperazinyl}butyrohydroxamic acid or hydrochloride salt thereof.

12. A composition of claim 4 including 3-{1-(4-phenyl)piperazinyl}propionohydroxamic acid or hydrochloride salt thereof.

13. A composition of claim 4 including 4-{1-(4-phenethyl)piperazinyl}-butyrohydroxamic acid or hydrochloride salt thereof.

14. A composition of claim 4 including {1-(4-phenethyl)piperazinyl}acetohydroxamic acid or hydrochloride salt thereof.

15. The composition of claim 4 wherein the compound is present in amounts from about 0.1 to about 10% wt.

* * * * *